United States Patent [19]

Connor et al.

[11] 4,076,729
[45] Feb. 28, 1978

[54] (4-OXO-4H-1-BENZOPYRAN-3-YL)AMINOOXOACETIC ACIDS AND THEIR DERIVATIVES

[75] Inventors: David T. Connor, Parsippany; Patricia A. Young, Madison; Max von Strandtmann, Rockaway, all of N.J.

[73] Assignee: Warner-Lambert Company, Morris Plains, N.J.

[21] Appl. No.: 710,996

[22] Filed: Aug. 2, 1976

[51] Int. Cl.² .................. C07D 311/02; C07D 311/72; A61K 31/35; A61K 31/355
[52] U.S. Cl. ............................ 260/345.2; 260/345.5; 424/283; 424/284
[58] Field of Search ............................ 260/345.2, 345.5

[56] References Cited

U.S. PATENT DOCUMENTS

| 3,862,143 | 1/1975 | Klutchko et al. | 260/345.2 |
| 3,906,005 | 9/1975 | Klutchko et al. | 260/345.2 |

*Primary Examiner*—Nicky Chan

*Attorney, Agent, or Firm*—Albert H. Graddis; Frank S. Chow

[57] ABSTRACT

The present invention relates to compounds of the formula:

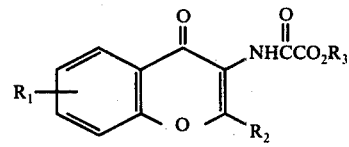

wherein $R_1$ is hydrogen, halogen, hydroxy, lower alkoxy or lower alkyl, $R_2$ is hydrogen or lower alkyl; $R_3$ is hydrogen or lower alkyl.

These compounds, including their corresponding pharmaceutically acceptable salts, are useful in the management of allergic conditions such as hay fever and as a prophylactic in the treatment of bronchial asthma.

9 Claims, No Drawings

(4-OXO-4H-1-BENZOPYRAN-3-YL)AMINOOXOACETIC ACIDS AND THEIR DERIVATIVES

The present invention relates to (4-oxo-4H-1-benzopyran-3-yl)aminooxoacetic acids and their derivatives having the following formula:

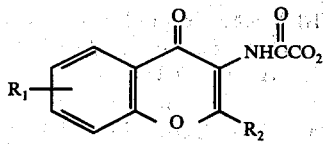

wherein $R_1$ is hydrogen, halogen, hydroxy, lower alkoxy or lower alkyl, $R_2$ is hydrogen or lower alkyl and $R_3$ is hydrogen or lower alkyl.

In the above definition for $R_1$–$R_3$ lower alkyl is meant to have 1–6 carbon atoms and includes, for example, methyl, ethyl, propyl, isopropyl, butyl, isobutyl and so on.

Halogen includes all the four members, i.e., chlorine, bromine, fluorine and iodine.

The present invention also includes within its scope the corresponding pharmaceutically acceptable salts of the above compounds as well as methods for the treatment of allergic conditions by the administration of the aforesaid compound in a pharmaceutical dosage form.

The compounds of this invention are active in prevention of allergic and asthmatic reactions in rats at dose levels of 0.5 mg/kg to 100 mg/kg; thus ethyl (6-chloro-4-oxo-4H-1-benzopyran-3-yl)aminooxoacetate shows a 92% inhibition of the allergic response at 10 mg/kg when tested intraperitoneally in the passive cutaneous anaphalaxis (PCA) screen, which is a modification of procedures described by I. Mota, *Life Sciences*, 7: 465 (1963) and Z. Ovary and O. Bier, *Proc. Soc. Exptl. Biol. Med.*, 81: 585 (1952). Similarly, (6-chloro-4-oxo-4H-1-benzopyran-3-yl)aminooxoacetic acid shows a 41% inhibition of the allergic response at 0.5 mg/kg when tested intravenously in the PCA screen. Consequently, they are indicated in the management of asthma, hay fever and other allergic conditions.

Generally speaking, for the treatment of bronchial asthma, a dose of about 1–100 mg/kg orally or by parenteral administration is suggested. This dosage regimen may be varied depending upon the age, sex, weight of the patient and the severity of the condition being treated, by methods well-known to the healing arts.

The compounds of this invention and their salts may also be administered by inhalation in which the compounds are inhaled directly in the form of an aerosol.

The pharmaceutical dosage forms for the administration of the instant compounds are tablets, capsules and aqueous suspensions. These dosage forms are prepared by combining the active ingredient with pharmaceutical diluents such as lactose and compounded into tablets by well-known tabletting technology. The active ingredient in the finished dosage form is from 1–100 mg per unit.

According to the present invention, Compound I is prepared by the following reaction scheme:

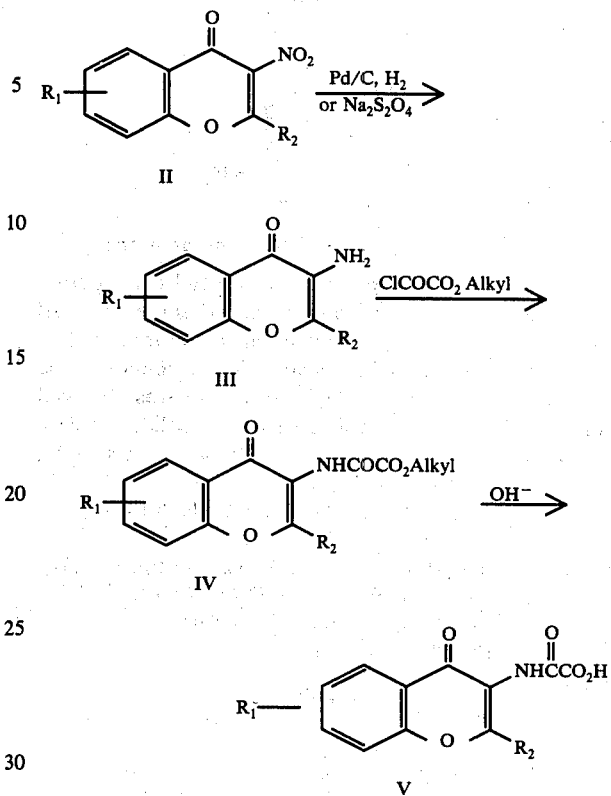

The starting materials are prepared by the following procedure:

2-Methyl-3-nitro-4H-1-benzopyran-4-one and 3-aminochromone by the method of G. J. P. Beckett and G. P. Ellis, *Tetrahedron Letters*, 719 (1976); 3-amino-6-chlorochromone by the method of M. von Strandtmann and S. Klutchko, U.S. Pat. No. 3,906,005, and ethyl oxalyl chloride is available from Aldrich Chemical Company.

Briefly, Compound II is prepared by hydrogenating Compound II by a known hydrogenation procedure, e.g., palladium on charcoal under an atmosphere of hydrogen. Compound IV, in turn, is readily obtained by treatment with an alkyl oxalyl halide at ambient temperature. The corresponding acid, V, is prepared by hydrolysis in a manner known per se.

Esters corresponding to Compound V are also prepared in a manner per se.

For more detailed description of the preparation of the instant compounds, please refer to the following examples. The pharmaceutically acceptable salts of the present invention are prepared by reacting Compound I (wherein $R_3$=H) with bases such as sodium, potassium and calcium hydroxides or bicarbonates in stoichiometric amounts, and they may also be prepared by reacting with organic bases such as amines. The salts thus formed are recovered by methods well-known in the art.

In order to illustrate the practice of the invention, the following examples are included. In the examples, temperatures are in degrees Centigrade.

EXAMPLE 1

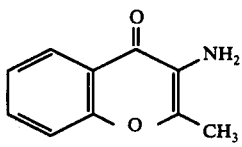

2-Methyl-3-amino-4H-1-benzopyran-4-one

A mixture of 2-methyl-3-nitro-4H-1-benzopyran-4-one (5.0g, 0.244 mole) and 10% palladium on charcoal (0.75g) in ethanol (250 ml) was shaken under a hydrogen atmosphere in a Parr shaker for 40 minutes. The catalyst was filtered off, and the solvent was removed under reduced pressure to give yellow solids. Recrystallization from benzene gave yellow crystals (2.4g, 56%), m.p. 118°–20° C.

Anal. Calcd. for $C_{10}H_9NO_2$: C, 68.56; H, 5.18; N, 8.00. Found: C, 68.47; H, 5.23; N, 7.96.

NMR (CDCl$_3$) δ 8.2 (md, 1, ArH), 7.42 (m, 3, ArH), 3.40 (b.s, 2, NH$_2$, exchange with D$_2$O), 2.40 (s, 3, CH$_3$).

IR 3410, 3320 (NH$_2$), 1640cm$^{-1}$ (CO).

UV 235 (20,720), 330 (5,680).

EXAMPLE 2

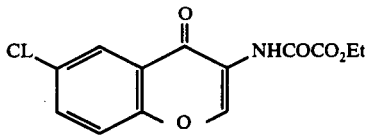

Ethyl (6-chloro-4-oxo-4H-1-benzopyran-3-yl)aminooxoacetate

Ethyl oxalyl chloride (1.36g, 0.01 mole) was added dropwise to a solution of 3-amino-6-chlorochromone (1.95g, 0.01 mole) and pyridine (1.58g, 0.02 mole) in methylene chloride (100 ml). The resulting homogeneous solution was stirred at room temperature for 90 minutes. The solvent was evaporated at reduced pressure to give a yellow solid. The solid was triturated with water, filtered and dried. Recrystallization from ethanol gave white crystals, (2.3g, 78%), m.p. 161°–162°.

Anal. Calcd. for $C_{13}H_{10}ClNO_5$: C, 52.81; H, 3.41; N, 4.74; Cl, 11.99. Found: C, 52.93; H, 3.28; N, 4.85; Cl, 12.06.

NMR (CDCl$_3$) δ 9.55 (bs, 1, N-H, exchanges with D$_2$O), 9.40 (s, 1, C$_2$H), 8.2 (d, 1, ArH), 7.61 (m, 2, ArH), 4.45 (q, 2, OCH$_2$) and 1.43 (t, 3, CH$_3$).

IR 3370 (NH), 1750 (CO), 1710 (CO), 1650cm$^{-1}$ (CO).

UV 220 (17,000), 270 (16,000), 310 (8,000).

EXAMPLE 3

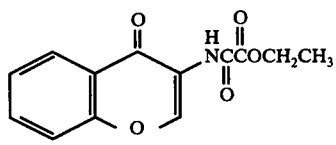

Ethyl (4-oxo-4H-1-benzopyran-3-yl)aminooxoacetate

Prepared by the method used for Example 2 from aminochromone (20g, 0.248 mole). Recrystallization of the yellow solids from absolute ethanol gave light brown crystals (23.0g, 71%), m.p. 146.5°–48° C.

Anal. Calcd. for $C_{13}H_{11}NO_5$: C, 59.77; H, 4.24; N, 5.36. Found: C, 59.50; H, 4.36; N, 5.27.

NMR (CDCl$_3$) δ 9.60 (bs, 1, NH, exchanges with D$_2$O), 9.40 (s, 1, C$_2$H), 8.25 (d, 1, ArH), 7.57 (m, 3, ArH), 4.44 (q, 2, CH$_2$, J = 7Hz), 1.42 (t, 3, CH$_3$, J = 7Hz).

IR 3380 (NH), 1763 (CO), 1715 (CO), 1639cm$^{-1}$ (CO).

UV 218 (16,120), 266 (15,440), 303 (9,800).

EXAMPLE 4

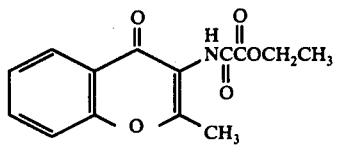

Ethyl (2-methyl-4-oxo-4H-1-benzopyran-3-yl)aminooxoacetate

Prepared by the method described for Example 2 from 2-methyl-3-amino-4H-1-benzopyran-4-one (2.0g, 0.0114 mole). Recrystallization from benzene/hexane gave white crystals (2.05g, 63%), m.p. 100°–04° C.

Anal. Calcd. for $C_{14}H_{13}NO_5$: C, 61.09; H, 4.76; N, 5.09. Found: C, 60.83; H, 4.68; N, 5.04.

NMR (CDCl$_3$) δ 8.90 (bs, 1, NH, exchanges with D$_2$O), 8.18 (md, 1, ArH), 8.4-7.2 (m, 3, ArH), 4.43 (q, 2, CH$_2$, J = 7Hz), 2.46 (s, 3, CH$_3$), 1.46 (t, 3, CH$_3$, J = 7Hz).

IR 3380 (NH), 1765 (CO), 1718 (CO), 1640cm$^{-1}$ (CO).

UV 223 (20,760), 297 (7,400).

EXAMPLE 5

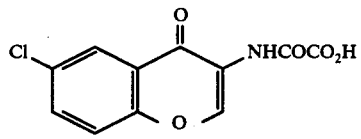

(6-Chloro-4-oxo-4H-1-benzopyran-3-yl)aminooxoacetic acid

Ethyl (6-chloro-4-oxo-4H-1-benzopyran-3-yl)aminooxoacetate (2.7g, 0.92 mole) was suspended in ethanol (100 ml) and water (100 ml). 0.1N sodium hydroxide solution was added dropwise, with occasional warming on a steam bath, until the reaction mixture remained slightly basic. The color of the mixture changed to orange on addition of the base and then back to white. The sodium hydroxide solution was added until a faint orange color persisted. The product was filtered off, triturated with 1N hydrochloric acid, washed with water and sucked dry on filter. Recrystallization from methanol gave white crystals (2,3g, 94%), m.p. 213°–215° C.

Anal. Calcd. for $C_{11}H_6ClNO_5$: C, 49.37; H, 2.26; N, 5.23; Cl, 13.25. Found: C, 49.53; H, 2.38; N, 5.19; Cl, 13.42.

NMR (DMSO) δ 9.6 (bs, 1, N-H, exchanges with $D_2O$), 9.20 (s, 1, $C_2H$), 8.2-7.5 (m, 3, ArH).

IR 3420 (N-H), 2800-2500 (OH), 1750 (CO), 1650cm$^{-1}$ (CO).

UV 214 (21,000), 263 (28,500), 320 (9,000).

EXAMPLE 6

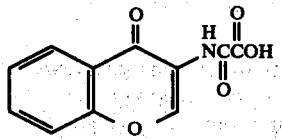

(4-Oxo-4H-1-benzopyran-3-yl)aminooxoacetic acid

Prepared by the method described for Example 5 from ethyl (4-Oxo-4H-1-benzopyran-3-yl)aminooxoacetate (15.5g, 0.6 mole). Recrystallization from absolute ethanol gave off-white crystals (7.4g, 53.6%), m.p. 195°-97° C.

Anal. Calcd. for $C_{11}H_7NO_5$: C, 56.66; H, 3.03; N, 6.01. Found: C, 56.60; H, 3.06; N, 5.87.

NMR (DMSO) δ 9.63 (bs, 1, NH, exchanges with $D_2O$), 9.23 (s, 1, $C_2H$), 8.15 (md, 1, ArH), 7.75 (m, 3, ArH).

IR 3340 (NH), 3110 (OH broad), 1770 (CO), 1699 (CO), 1628cm$^{-1}$ (CO).

UV 213 (15,200), 253 (20,200), 309 (7,320).

EXAMPLE 7

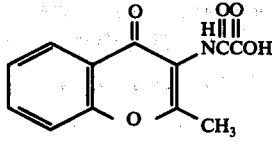

(2-Methyl-4-oxo-4H-1-benzopyran-3-yl)aminooxoacetic acid

Prepared by the method described for Example 5 from ethyl (2-methyl-4-oxo-4H-1-benzopyran-3-yl)aminooxoacetate (1.0g, 0.00364 mole). Recrystallization from absolute ethanol gave white crystals (0.47g, 56%), m.p. 208°-09° C.

Anal. Calcd. for $C_{12}H_9NO_5$: C, 58.30; H, 3.67; N, 5.67. Found: C, 58.34; H, 3.77; N, 5.54.

NMR (DMSO) δ 10.01 (s, 1, NH, exchanges with $D_2O$), 8.3-7.3 (m, 4, ArH), 2.40 (s, 3, $CH_3$).

IR 3210 (NH), 2800-2200 (broad COOH), 1742 (CO), 1705 (CO), 1690cm$^{-1}$ (CO).

UV 228 (19,480), 299 (7,200).

EXAMPLE 8

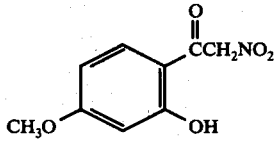

1-(2-Hydroxy-4-methoxyphenyl)-2-nitro ethanone

3-Nitro-4-hydroxy-7-methoxy coumarin (1.85 g, 0.078 m), prepared as described in D. R. Buckle, et al., J. Med. Chem., 18, 391 (1975), was stirred at room temperature in 5% aqueous sodium hydroxide (60 ml) for 20 hours. The mixture was slowly acidified with 5N HCl. The product was filtered off and sucked dry. Recrystallization from absolute ethanol gave pale yellow crystals (0.92 g, 56%), m.p. 138°-40° C.

Anal. Calcd. for $C_9H_9NO_5$: C, 51.19; H, 4.30; N, 6.63. Found: C, 51.10; H, 4.35; N, 6.52.

NMR (DMSO) δ 11.41 (b.s. 1, OH, exchanges with $D_2O$), 7.77 (d, 1, $C_6H$), 6.65 (m, 2, $C_3H$ and $C_5H$), 6.20 (s, 2, $CH_2$, exchanges with $D_2O$), 3.86 (s, 3, $OCH_3$).

IR 1625cm$^{-1}$ CO

UV 208 (16,800) shoulder; 227 (9.460) shoulder; 278 (11,000), 313 (7,000), 371 (6,560).

EXAMPLE 9

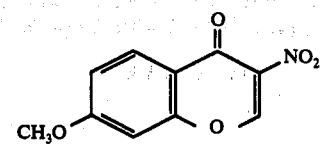

3-Nitro-7-methoxy-4H-1-benzopyran-4-one was prepared by the addition of 1-(2-hydroxy-4-methoxyphenyl)-2nitro ethanone (2.11 g, 0.01m), prepared in Example 8, and sodium formate (0.68 g, 0.01m) to stirred acetic-formic anhydride (25 ml). The reaction was warmed to 80° C. and allowed to return to room temperature. After stirring at least an additional 1 hour, cold water (100 ml) was added. The product was filtered off, washed with fresh portions of water and sucked dry. Recrystallization from ethyl acetate gave yellow crystals (1.7 g, 77.5%), m.p. 185°-87° C.

NMR (DMSO) δ 9.55 (s, 1, $C_2H$), 8.05 (d, 1, $C_5H$), 7.20 (m, 2, $C_6H$ and $C_8H$), 3.95 (s, 3, $OCH_3$).

EXAMPLE 10

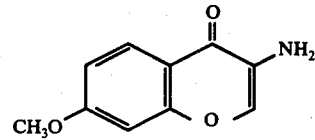

3-Amino-7-methoxy-4H-1-benzopyran-4-one

Sodium dithionite (20g) was added to a stirred suspension of 3-nitro-7-methoxy-4H-1-benzopyran-4-one (7.0 g, 0.0316 m) in absolute ethanol (80 ml) and water (30 ml). The reaction mixture was stirred under nitrogen for 20 min. The solvents were removed under reduced pressure to give a solid residue. The residue was dissolved in water and extracted with chloroform. The chloroform extracts were dried over sodium sulfate and evaporated to give 3-amino-7-methoxy-4H-1-benzopyran-4-one (4.5 g, 78.5%), m.p. 143°-146°.

EXAMPLE 11

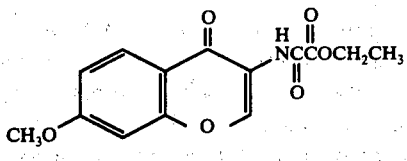

Ethyl (7-methoxy-4-oxo-4H-1-benzopyran-3-yl)aminooxoacetate

This was prepared by the method described in Example 2 from 3-amino-7-methoxy-4H-1-benzopyran-4-one (5 g, 0.0261 m). Recrystallization from ethyl acetate gave white crystals (3.6 g, 47.4%), m.p. 218°–20° C.

Anal. Calcd. for $C_{14}H_{13}NO_6$: C, 57.73; H, 4.50; N, 4.82. Found: C, 57.54; H, 4.59; N, 4.82.

NMR (TFA) δ 9.50 (s, 1, $C_2H$), 8.25 (d, 1, $C_5H$), 7.25 (m, 2, $C_6H$ and $C_8H$), 4.61 (q, 2, $CH_2$, J = 7Hz), 4.10 (s, 3, $OCH_3$), 1.55 (t, 3, $CH_3$, J = 7Hz).

IR 3350cm$^{-1}$ NH; 1730, 1690, 1650cm$^{-1}$ CO
UV 221 (13,840), 250 (17,480), 275 (19,920).

EXAMPLE 12

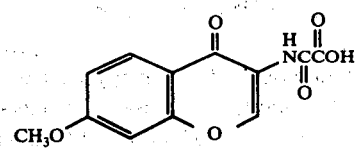

(7-Methoxy-4-oxo-4H-1-benzopyran-3-yl)aminooxoacetic acid

This was prepared by the method described in Example 5 from ethyl (7-methoxy-4-oxo-4H-1-benzopyran-3-yl)aminooxoacetate (2.1 g, 0.0723 m). Recrystallization from absolute ethanol gave white crystals (1.3 g, 68%), m.p. 236°–38° C.

Anal. Calcd. for $C_{12}H_9NO_6$: C, 54.76; H, 3.45; N, 5.32. Found: C, 54.60; H, 3.48; N, 5.14.

We claim:

1. A compound of the formula:

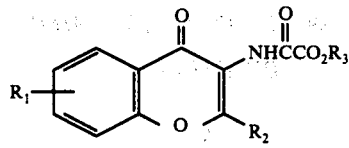

wherein $R_1$ is hydrogen, halogen, lower alkoxy or lower alkyl; $R_2$ is hydrogen or lower alkyl; $R_3$ is hydrogen or lower alkyl and the corresponding pharmaceutically acceptable salts thereof.

2. A compound according to claim 1 which is ethyl (6-chloro-4-oxo-4H-1-benzopyran-3-yl)aminooxoacetate.

3. A compound according to claim 1 which is ethyl (4-oxo-4H-1-benzopyran-3-yl)aminooxoacetate.

4. A compound according to claim 1 which is ethyl (2-methyl-4-oxo-4H-1-benzopyran-3-yl)aminooxoacetate.

5. A compound according to claim 1 which is (6-chloro-4-oxo-4H-1-benzopyran-3-yl)aminooxoacetic acid.

6. A compound according to claim 1 which is (4-oxo-4H-1-benzopyran-3-yl)aminooxoacetic acid.

7. A compound according to claim 1 which is (2-methyl-4-oxo-4H-1-benzopyran-3-yl)aminooxoacetic acid.

8. A compound according to claim 1 which is ethyl (7-methoxy-4-oxo-4H-1-benzopyran-3-yl)aminooxoacetate.

9. A compound according to claim 1 which is (7-methoxy-4-oxo-4H-1-benzopyran-3-yl)aminooxoacetic acid.